United States Patent [19]

Hattori et al.

[11] Patent Number: 6,026,686
[45] Date of Patent: Feb. 22, 2000

[54] ARTICLE INSPECTION APPARATUS

[75] Inventors: Ichiro Hattori; Isamu Kawai; Akira Suzuki, all of Yokohama, Japan

[73] Assignee: Fujitsu Limited, Kawasaki, Japan

[21] Appl. No.: 08/941,106

[22] Filed: Sep. 30, 1997

[30] Foreign Application Priority Data

Mar. 19, 1997 [JP] Japan .................................. 9-066190

[51] Int. Cl.[7] .................................................. G01N 29/12
[52] U.S. Cl. ............................. 73/579; 702/56; 702/82
[58] Field of Search ............................ 73/579, 52, 12.01;
702/39, 34, 56, 81, 82

[56] References Cited

U.S. PATENT DOCUMENTS

| | | | |
|---|---|---|---|
| 2,635,746 | 4/1953 | Gordon | 73/579 |
| 3,438,493 | 4/1969 | Goble | 73/579 |
| 3,580,056 | 5/1971 | Warner | 73/579 |
| 3,623,358 | 11/1971 | Sugimoto | 73/579 |
| 4,166,393 | 9/1979 | Lindner et al. | 73/579 |
| 4,212,205 | 7/1980 | West et al. | 73/579 |
| 4,406,157 | 9/1983 | Miyahara et al. | 73/52 |
| 4,884,696 | 12/1989 | Peleg | 209/545 |
| 5,216,921 | 6/1993 | Tsuboi | 73/579 |
| 5,585,567 | 12/1996 | Van Manen | 73/579 |

Primary Examiner—Hezron Williams
Assistant Examiner—Rose M. Miller
Attorney, Agent, or Firm—Staas & Halsey LLP

[57] ABSTRACT

An article inspection apparatus is capable of inspecting an article which cannot be sorted out by image processing or a diagnostic process that employs energy to be transmitted through the article. A hitting sound is generated by a hitting sound generating device when an article is hit, and is detected by a sound detecting device and analyzed by a detected-sound analyzer. The analyzed result is converted into a pattern by a detected-sound pattern generator, and the pattern is matched with registered reference patterns from a reference pattern registering device by a pattern matching device. Based on the result of matching, the article is sorted out by an article sorting device. It is possible to detect the material of a container, such as cans of aluminum and iron which are identical in shape and size to each other. It is also possible to check the amount of a substance in a container that cannot directly be seen, or inspect baked articles for pores contained therein.

13 Claims, 11 Drawing Sheets

ARTICLE INSPECTION APPARATUS

BACKGROUND OF THE INVENTION (1) Field of the Invention

The present invention relates to an article inspection apparatus, and more particularly to an article inspection apparatus for sorting out articles that cannot be distinguished by appearance, based on different materials thereof or different net weights thereof.

(2) Description of the Related Art

It has heretofore been the customary practice to inspect articles that have been manufactured to ascertain whether they are defective or not. Primarily, products have been sorted out by determining if their appearance suffers deformation, damage, cracks, etc., or if any contents thereof have been filled up to a required level. Depending on whether products are to be sorted out on the basis of their appearance or contents, there have been employed various inspection processes.

Optical inspection processes have been employed in order to sort out articles according to their appearance. For example, a light beam or a laser beam is applied to an article, and a beam reflected or blocked by the article is detected. The reflected or blocked beam is processed by an image processing technique to recognize the shape or size of the article. The recognized shape or size of the article is compared with a reference shape pattern to determine whether the article is defective or not. If the recognized shape or size of the article is different from the reference shape pattern, then the article is judged as a defective article. According to another optical inspection process, the reflectance of a beam reflected from an article is measured, and the article is analyzed and sorted out on the basis of the measured reflectance.

To inspect an article for its content, there have been employed diagnostic processes for passing an X-ray or an ultrasonic wave through the article. The content of an article is determined according to the results of such a diagnostic process, and the determined content is used to sort out the article.

Empty can retrievers need to sort out empty cans according to their materials because they look exactly alike but are made of different materials such as aluminum and iron. Generally, an inspection process using a magnet is employed to sort out aluminum and iron cans. Another inspection process for sorting out aluminum and iron cans relies upon different load currents of an electric motor that is used to crush the aluminum and iron cans, as disclosed in Japanese patent publication No. 7-89388.

The image processing technique for recognizing article shapes is generally time-consuming for recognition processing. For example, inspecting a glass article for flaws on its surface requires a long inspection time as the entire surface needs to be inspected. Some articles cannot be inspected for their contents by the X-ray or ultrasonic diagnostic process. For example, the X-ray or ultrasonic diagnostic process cannot be used to inspect articles whose contents will be modified or adversely affected by being irradiated with X-rays or ultrasonic energy, and baked articles such as sintered bricks for minute internal pores contained therein.

SUMMARY OF THE INVENTION

It is an object of the present invention to provide an article inspection apparatus which can inspect articles in a short period of time for sorting them out, does not adversely affect articles that are inspected thereby, and can inspect articles such as baked articles for sorting them out.

To achieve the above object, there is provided an article inspection apparatus comprising hitting sound generating means for hitting an article to generate a hitting sound, and article identifying means for identifying the article based on the hitting sound generated by the hitting sound generating means.

The above and other objects, features and advantages of the present invention will become apparent from the following description when taken in conjunction with the accompanying drawings which illustrate a preferred embodiment of the present invention by way of example.

DETAILED DESCRIPTION OF THE PREFERRED EMBODIMENT

The principles of an article inspection apparatus according to the present invention will first be described with reference to FIG. 1.

Figure 1:
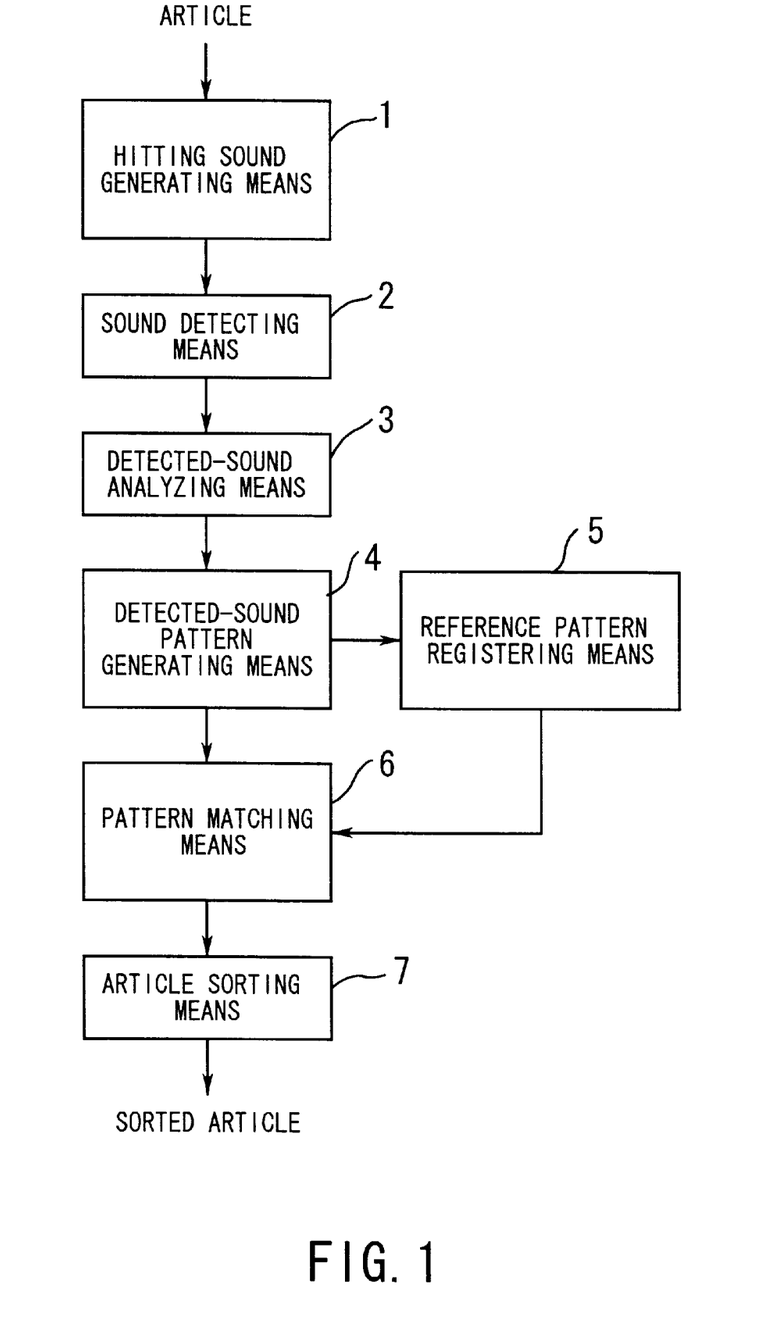
FIG. 1 is a block diagram illustrative of the principles of an article inspection apparatus according to the present invention.

As shown in FIG. 1, the article inspection apparatus has a hitting sound generating means 1 for hitting an article to be inspected to generate a hitting sound, a 10 sound detecting means 2 for detecting a hitting sound generated by the hitting sound generating means 1, a detected-sound analyzing means 3 for analyzing a sound detected by the sound detecting means 2, a detected-sound pattern generating means 4 for generating a pattern of a detected sound analyzed by the detected-sound analyzing means 3, a reference pattern registering means 5 for registering reference patterns of as many detected sounds as different types of articles, a pattern matching means 6 for matching a pattern generated by the detected-sound pattern generating means 4 with the reference patterns registered by the reference pattern registering means 5, and an article sorting means 7 for sorting out articles according to a result of pattern matching produced by the pattern matching means 6.

The article inspection apparatus operates as follows: First, the hitting sound generating means 1, the sound detecting means 2, the detected-sound analyzing means 3, and the detected-sound pattern generating means 4 are used to generate reference patterns of as many detected sounds as different types of articles, and the generated reference patterns are registered by the reference pattern registering means 5. Each of the reference patterns may comprise a pattern of a typical sound which is most representative of features of an article or a pattern of the average of a plurality of hitting sounds produced by articles of the same type or a plurality of samples of a hitting sound produced by an article.

An article to be inspected is supplied to the hitting sound generating means 1. The article supplied to the hitting sound generating means 1 is hit by a hammer and hence produces a hitting sound. The material of the hammer, the strength of the hit, the position where the article is hit by the hammer, and the time for which the article is hit by the hammer are selected depending on the article to be inspected. When a hitting sound is to be produced by an article, the article is surrounded by a sound-resistant cover so that ambient sound will not be introduced at the same time that the hitting sound is picked up. The hitting sound generated by the hitting sound generating means 1 is detected by the sound detecting means 2, which supplies the detected hitting sound to the detected-sound analyzing means 3. The detected-sound analyzing means 3 analyzes the supplied hitting sound and extract sound features inherent in the article. The sound features produced by the detected-sound analyzing means 3 is supplied to the detected-sound pattern generating means 4, which converts the supplied sound features into a pattern that is supplied to the pattern matching means 6. The pattern matching means 6 matches the pattern supplied from the detected-sound pattern generating means 4 with the reference patterns registered by and supplied from the reference pattern registering means 5 to determine which one of the reference patterns is close to the pattern supplied from the detected-sound pattern generating means 4. The result of matching from the pattern matching means 6 is supplied to the article sorting means 7, which sorts out the article according to the supplied result.

According to the present invention, comparable features of an article are checked using a hitting sound that is produced by the article when it is hit. The hitting sound produced by the article is characteristic of the material, shape, and dimensions of the article, and the type and amount of the content of the article. Therefore, the hitting sounds produced by articles can be used to sort out those articles which are made of different materials or have different amounts of contents that cannot be distinguished by their appearance.

A can material sorting apparatus for sorting out and collecting empty cans of aluminum and iron which are of the same shape and size, to which the principles of the present invention are applied, will be described below.

Figure 2:
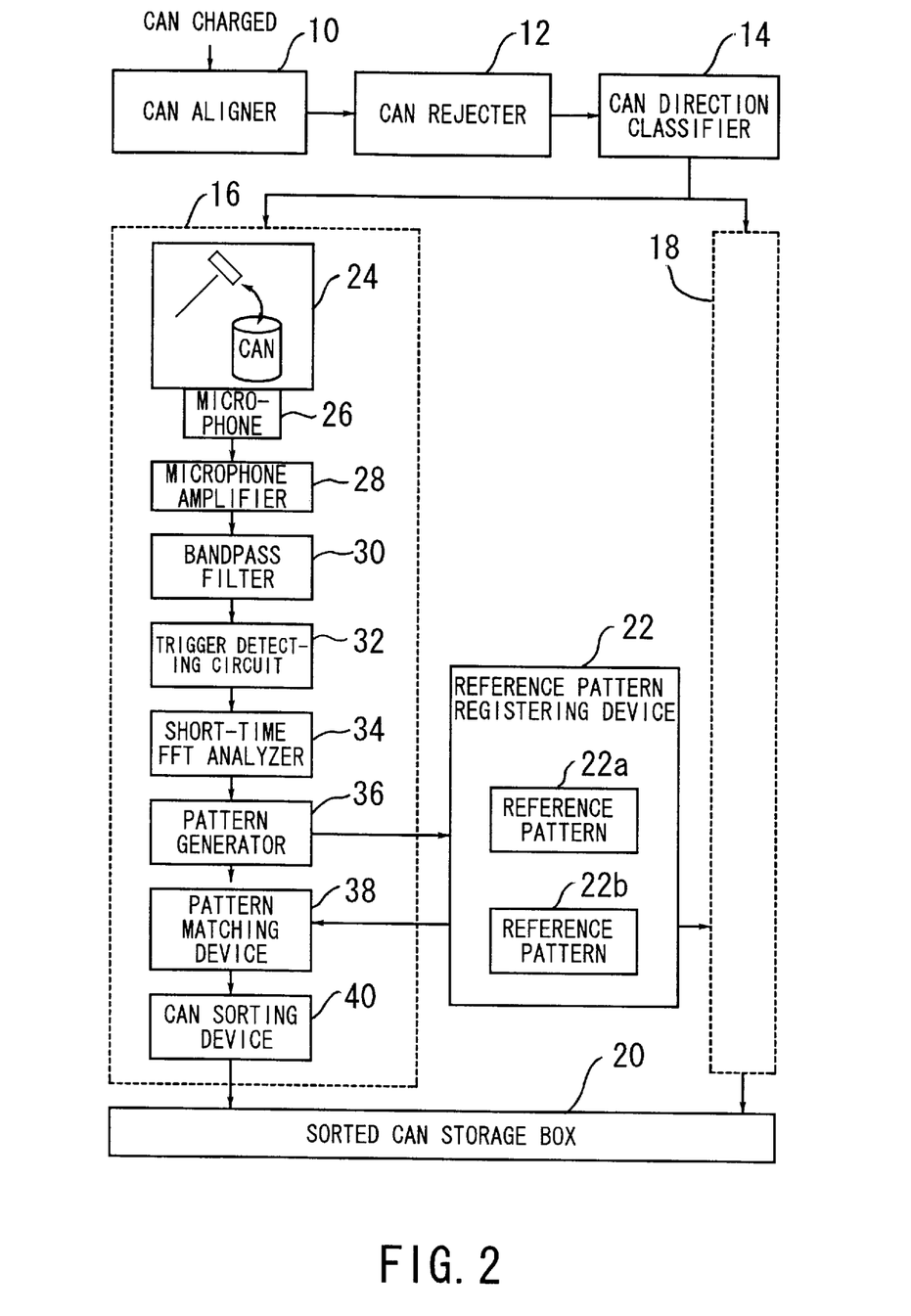
FIG. 2 is a block diagram of a can material sorting apparatus.

FIG. 2 shows the can material sorting apparatus in block form. As shown in FIG. 2, the can material sorting apparatus has a can aligner 10 for aligning empty cans of aluminum and iron that are charged into the can material sorting apparatus. The can aligner 10 has an outlet connected to a can rejecter 12 for rejecting empty cans that cannot be sorted out and a can direction classifier 14 for separating empty cans into a first group in which the empty cans have their ends facing in one direction and a second group in which the empty cans have their ends facing in the opposite direction. The ends of empty cans have holes or apertures produced when pull-tabs were removed therefrom, and will not be hit by a hammer to produce a hitting sound. The bottoms of empty cans, which are opposite to the ends thereof, are closed and will be hit by a hammer to produce a hitting sound. The can direction classifier 14 has an outlet connected to two can processors 16, 18 for processing empty cans supplied in the first and second groups, respectively. Since the two can processors 16, 18 are used, the can material sorting apparatus can process empty cans efficiently in a relatively short period of time. The can processors 16, 18 have respective outlets connected to a sorted can storage box 20. A reference pattern registering device 22 is connected to the can processors 16, 18. The reference pattern registering device 22 serves as the reference pattern registering means 5 shown in FIG. 1.

Since the can processors 16, 18 are structurally and functionally identical to each other, only the can processor 16 will be described below.

The can processor 16 has a can hitting device 24 for hitting an empty can that is supplied from the can direction classifier 14. The can hitting device 24 has a microphone 26 for detecting a hitting sound produced when the empty can is hit by a hammer. The microphone 26 has an output terminal connected to a microphone amplifier 28. The microphone amplifier 28 has an AGC (automatic gain control) circuit for eliminating level differences between hitting sounds produced by different empty cans. The microphone amplifier 28 has an output terminal connected to a bandpass filter 30 which removes ambient background noise that is picked up by the microphone 26. The bandpass filter 30 has upper and lower cutoff frequencies that are determined by signal components of hitting sounds. The microphone 26, the microphone amplifier 28, and the bandpass filter 30 jointly serve as the sound detecting means 2 shown in FIG. 1.

The bandpass filter 30 has an output terminal connected to a trigger detecting circuit 32 and a short-time FFT (fast Fourier transform) analyzer 34 which jointly serve as the detected-sound analyzing means 3 shown in FIG. 1. The short-time FFT analyzer 34 has an output terminal connected to a pattern generator 36 serving as the detected-sound pattern generating means 4 shown in FIG. 1. The pattern generator 36 has an output terminal connected to an input terminal of a pattern matching device 38 and another output terminal connected to a registering input terminal of the reference pattern registering device 22. The pattern matching device 38 has another input terminal 5 connected to an output terminal of the reference pattern registering device 22. The pattern matching device 38 serves as the pattern matching means 6 shown in FIG. 1. The pattern matching device 38 has an output terminal connected to a can sorting device 40 which serves as the article sorting means 7 shown in FIG. 1, the can sorting device 40 being coupled to the sorted can storage box 20.

The reference pattern registering device 22 stores as many reference patterns 22a, 22b registered therein as the number of can types to be processed. Since the can material sorting apparatus sorts out and collects empty cans of aluminum and iron which are of the same shape and size, the two reference patterns 22a, 22b are registered in the reference pattern registering device 22, the reference pattern 22a indicating a typical pattern of a hitting sound of aluminum cans and the reference pattern 22b a typical pattern of a hitting sound of iron cans.

Operation of the can material sorting apparatus will be described below.

Figure 3:
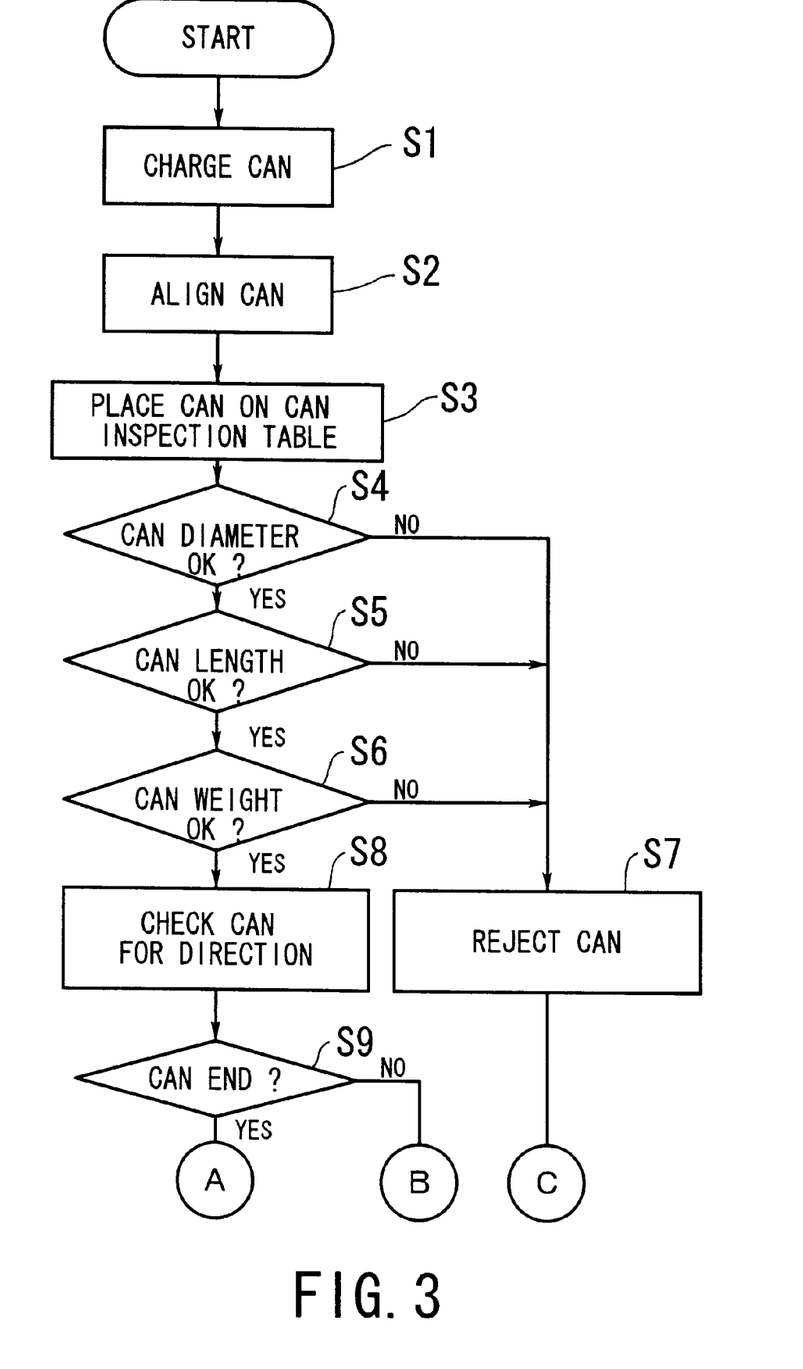
FIG. 3 is a flowchart of a pre-processing operation of the can material sorting apparatus.

FIG. 3 shows a pre-processing operation of the can material sorting apparatus. As shown in FIG. 3, empty cans are charged into a can inlet of the can aligner 10 in a step S1. The can aligner 10 aligns the charged empty cans into an array and delivers the aligned empty cans into the can rejecter 12 in a step S2. The can rejecter 12 checks whether each of the delivered empty cans can be sorted out, i.e., can be processed, by the can processor 16 or the can processor 18. Specifically, in order to check the successively delivered empty cans one by one, the can rejecter 12 places an empty can, one at a time, on an inspection table in a step S3, and checks the empty can for its diameter, length, and weight successively or at the same time in respective steps S4, S5, S6. The can rejecter 12 checks the empty can for its weight in order to determine whether the empty can still holds any remaining content or some foreign matter therein. If either one of the diameter, length, and weight of the checked can is not acceptable, then the can rejecter 12 judges the inspected empty can as a can that cannot be sorted out and rejects the empty can in a step S7. After or simultaneously checking the empty can for its diameter, length, and weight, the can rejecter 12 checks the empty can for its direction in a step S8. Thereafter, the empty can is delivered from the can rejecter 12 to the can direction classifier 14. The can direction classifier 14 determines whether the direction checked in the step S8 is toward the can end or not in a step S9, and determines, based on the determined result, whether the empty can is to be delivered to the can processor 16 or the can processor 18.

Figure 4:
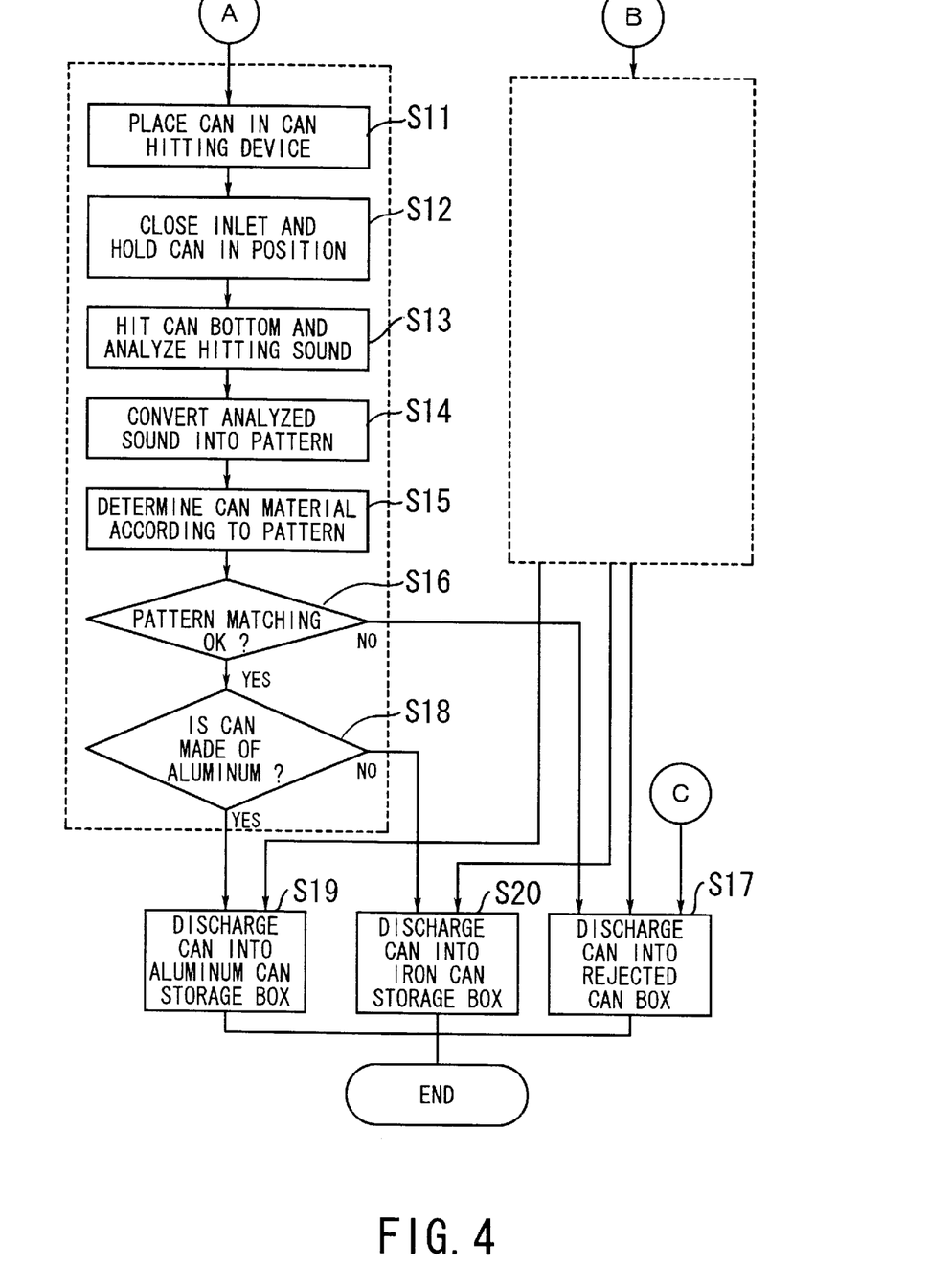
FIG. 4 is a flowchart of a sorting operation of the can material sorting apparatus.

FIG. 4 shows a sorting operation of the can material sorting apparatus, which is carried out by either one the can processors 16, 18. Since the can processors 16, 18 operate in the same way as each other, the operation of the can processor 16 will be described below. The empty can classified by the can direction classifier 14 is introduced into the can hitting device 24 though an inlet thereof in a step S11. The inlet of the can hitting device 24 is closed by a sound-resistant door and the empty can is held in position in a step S12. Then, the can hitting device 24 hits the bottom of the empty can with a hammer to produce a hitting sound, which is picked up and transmitted through the microphone 26, the microphone amplifier 28, the bandpass filter 30, and the trigger detecting circuit 32 to the short-time FFT analyzer 34. The short-time FFT analyzer 34 then analyzes the hitting sound in a step S13. An analyzed result produced by the short-time FFT analyzer 34 is supplied to the pattern generator 36, which converts the analyzed result into a pattern in a step S14. The generated pattern is supplied to the pattern matching device 38, which matches the supplied pattern with the reference patterns 22a, 22b that are registered in and supplied from the reference pattern registering device 22 in a step S15.

After the pattern matching in the pattern matching device 38, the empty can is delivered to the can sorting device 40. The can sorting device 40 determines whether the empty can has properly been matched for pattern by the pattern matching device 38 in a step S16. If the pattern matching device 38 has failed to determine clearly whether the empty can is made of aluminum or iron, then the can sorting device 40 rejects the empty can into a rejected can box in a step S17. If the inspected empty can is made of either aluminum or iron, then the can processor 16 determines whether the empty can is made of aluminum or not in a step S18. If the empty can is made of aluminum, then the can processor 16 discharges the empty can into an aluminum can storage box in a step S19. If the empty can is not made of aluminum, then the can processor 16 discharges the empty can into an iron can storage box in a step S20. When the empty can is judged as a can that cannot be sorted out and rejected in the step S7 of the pre-processing operation, the empty can is rejected into the rejected can box in the step S17.

A process of determining the material of an empty can according to the pattern matching based on the hitting sound generated by the can hitting device 24 will be described in detail below.

Figure 5:
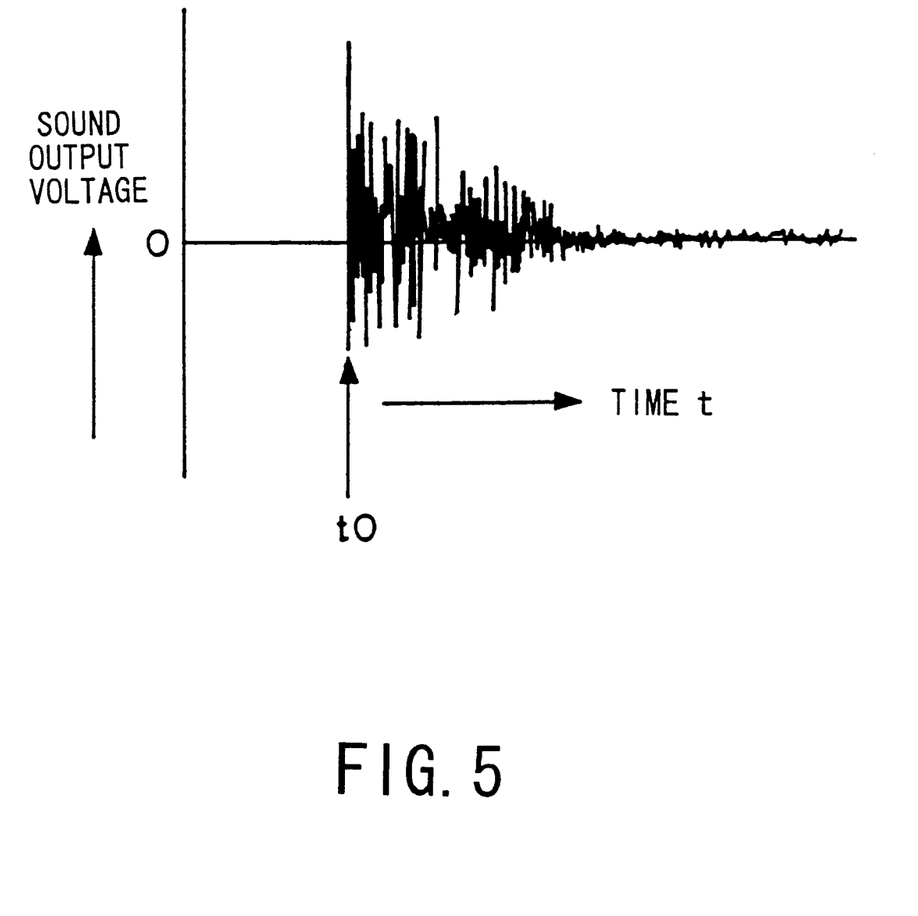
FIG. 5 is a diagram showing the waveform of a hitting sound produced by a can which is hit by a can hitting device.

FIG. 5 shows the waveform of a hitting sound produced by an empty can which is hit by the can hitting device 24. The hitting sound generated by the can hitting device 24 is picked up by the microphone 26, and the sound signal produced by the microphone 26 is amplified by the microphone amplifier 28, after which unwanted signal components are removed from the amplified signal by the bandpass filter 30. The bandpass filter 30 produces a sound signal having a large amplitude at a time t0, with the amplitude progressively decreasing with time, as shown in FIG. 5.

The sound signal produced by the bandpass filter 30 is supplied to the trigger detecting circuit 32, which detects the time t0 for the short-time FFT analyzer 34 to start analyzing the sound signal.

Figure 6:
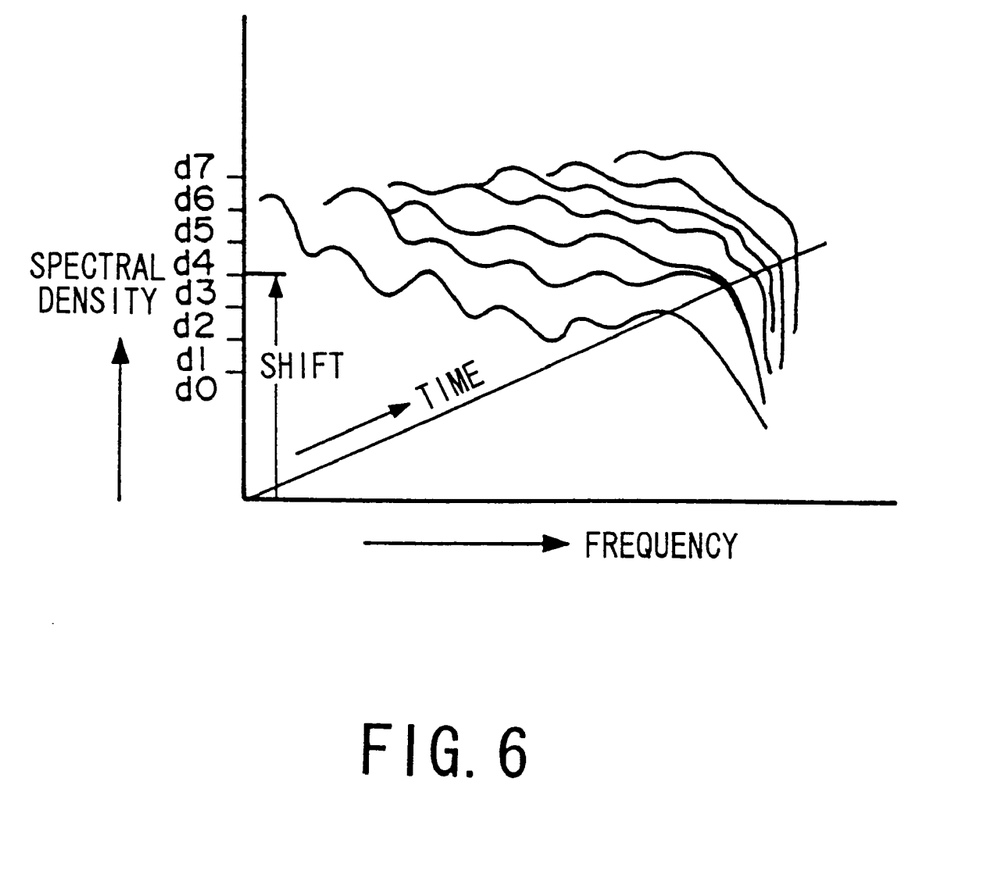
FIG. 6 is a diagram of a three-dimensional representation of the result of an analysis effected on a signal of the hitting sound by a short-time FFT analyzer.

FIG. 6 shows a three-dimensional representation of the result of an analysis effected on the signal of the hitting sound by the short-time FFT analyzer 34. The short-time FFT analyzer 34 analyzes the signal of the hitting sound to obtain the three-dimensional representation of the result of the analysis as shown in FIG. 6. In FIG. 6, the X-axis represents the frequency, the Y-axis represents time, and the Z-axis represents the spectral density. The frequency is shown in a linear or logarithmic scale, and the time is shown in a minute scale. The spectral density is shown in a linear scale such that a density capable of recognizing sound features, i.e., a quantized value d3 of the spectral density in FIG. 6, is shifted nearly to the center of the spectral density axis. The analyzed signal of the hitting sound is expressed as the spectral density which varies along the frequency varies continuously with time. The analyzed signal is converted into a pattern by the pattern generator 36.

Figure 7A:
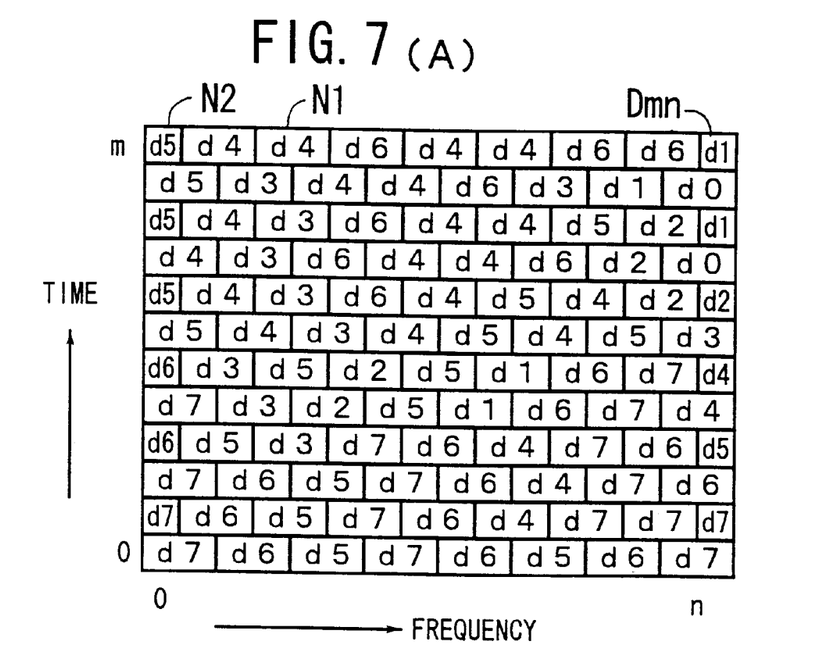
FIG. 7(A) is a diagram showing a detected-sound quantized pattern outputted by a pattern generator.
Figure 7B:
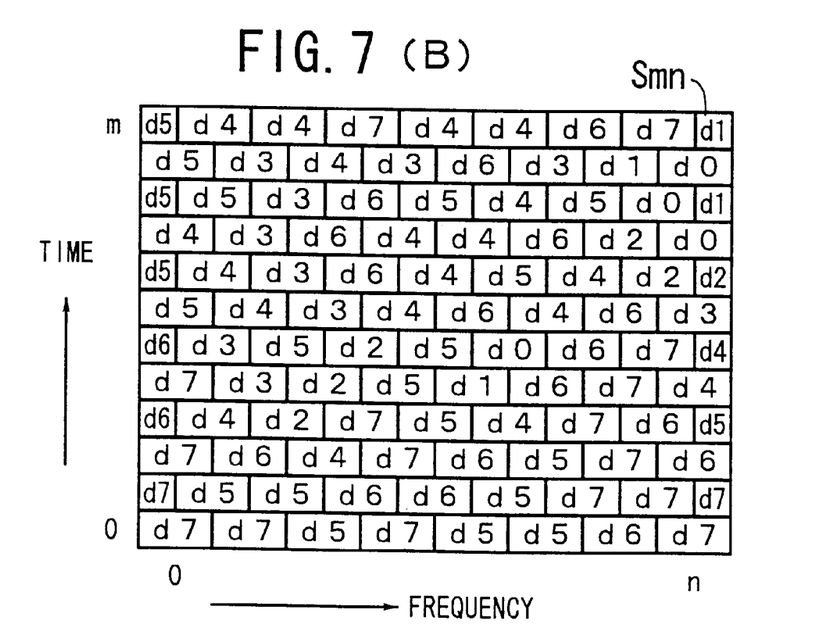
FIG. 7(B) is a diagram showing a registered reference quantized pattern.

FIGS. 7(A) and 7(B) show quantized patterns generated by the pattern generator 36. Specifically, FIG. 7(A) shows a detected-sound quantized pattern outputted by the pattern generator 36, and FIG. 7(B) shows a registered reference quantized pattern. The analyzed signal is converted into a pattern by dividing an X-Y plane formed by the frequency axis and the time axis into equal portions, each having a given width, along the time axis, then dividing the X-Y plane into equal portions, each having a given width, along the frequency axis, thereby producing a plurality of segments, and writing corresponding quantized values of the spectral density into the respective segments. However, in order to disperse feature data over segments that are adjacent to each other along the time axis, those segments that are adjacent to each other along the time axis are shifted along the frequency axis by a distance corresponding to half the size of a segment. Therefore, a quantized pattern comprises complete segments N1 and half segments N2 (having an area half the complete segments N1) that are present at upper and lower ends of the frequency range. The quantized value in each of the segments may be one of eight steps dn={d0, d2, . . . , d7}. The quantized value of a detected sound is represented by F(Dij)∈dn, and the quantized value of a registered reference quantized pattern by F(Sij)∈dn. After the detected hitting sound is thus converted into a pattern, the pattern is matched with the reference patterns by the pattern matching device 38.

Figure 8:
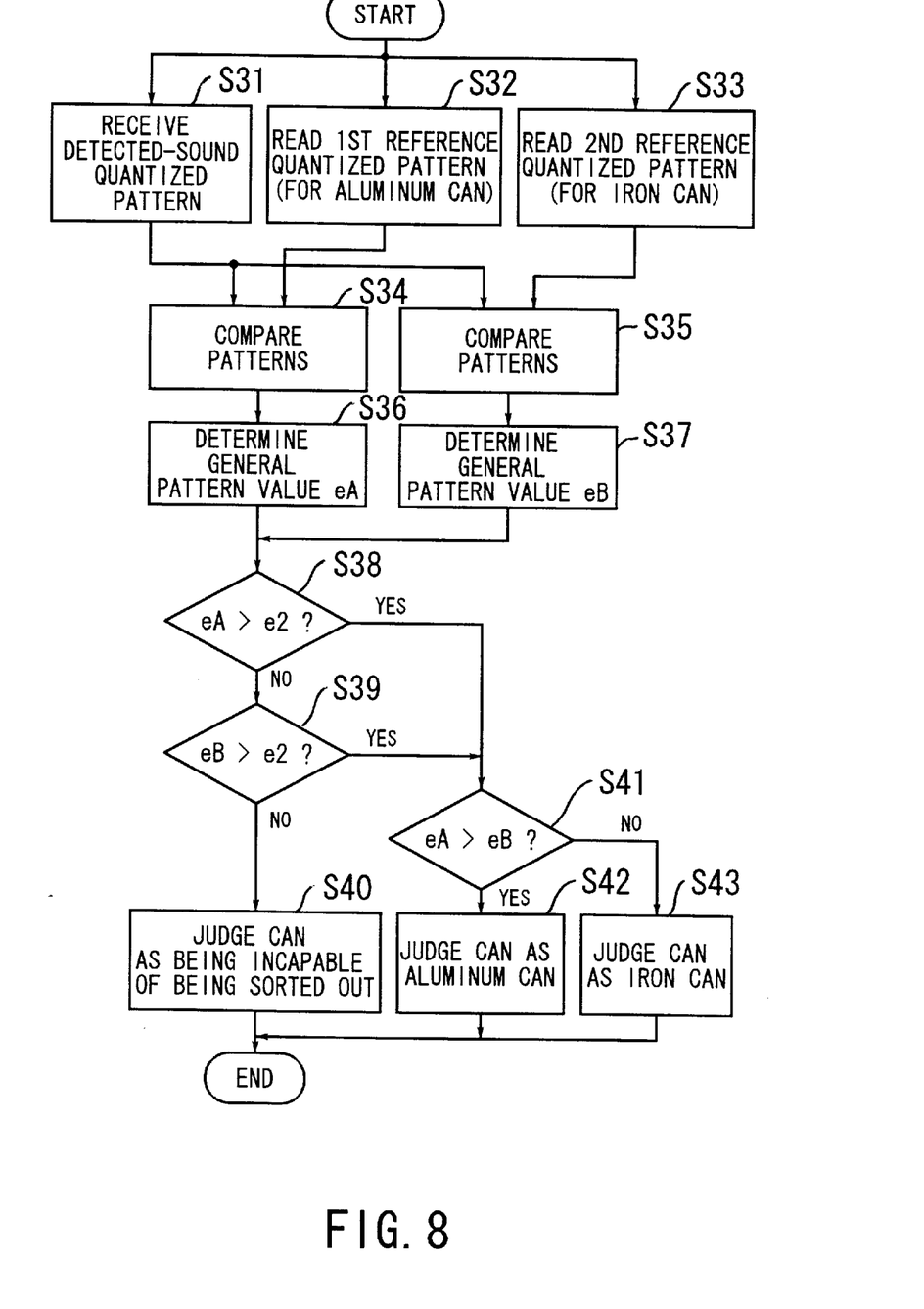
FIG. 8 is a flowchart of an operation sequence of a pattern matching device.

FIG. 8 shows an operation sequence of the pattern matching device 38. As shown in FIG. 8, the pattern matching device 38 receives the quantized pattern of a detected hitting sound from the pattern generator 36 in a step S31, and also reads the reference pattern 22a for aluminum cans as a first reference quantized pattern and the reference pattern 22b for iron cans as a second reference quantized pattern from the reference pattern registering device 22 in respective steps S32, S33. Then, the pattern matching device 38 compares the quantized pattern of the detected hitting sound with the reference pattern 22a in a step S34, and compares the quantized pattern of the detected hitting sound with the reference pattern 22b in a step S35. These pattern comparison steps are carried out as follows:

The quantized value of each of the segments of the quantized pattern of the detected hitting sound and the quantized value of each corresponding one of the segments of the first or second reference quantized pattern are compared with each other, and a difference $\Delta ij$ therebetween is determined by:

$$\Delta ij = |F(Dij) - F(Sij)| \tag{1}$$

If the difference $\Delta ij$ is equal to or smaller than a certain threshold el, i.e., if $\Delta ij \leq el$, then the compared quantized values of the segments are judged as being very similar to each other, and Nij=1 is assigned to the segment if it is a complete segment and Nij=½ is assigned to the segment if it is a half segment. If $\Delta ij > el$, then the compared quantized values of the segments are judged as being not essentially similar to each other, and Nij=0 is assigned to the segment irrespective of whether it is a complete segment or a half segment. The above process is carried out on all the segments.

Values Nij thus determined as representing the similarity for all the segments are accumulated into general pattern values eA, eB in steps S36, S37. These general pattern values eA, eB are calculated as follows:

$$eA, eB = \sum_{i=0, j=0}^{i=m, j=n} Nij / N \tag{2}$$

where N is the number of all segments, which is the sum of the total number of complete segments N1 and the total number of half segments N2.

Then, the general pattern value eA is compared with a given threshold e2 (0<e2<1) in a step S38. If the general pattern value eA is smaller than the threshold e2, then the general pattern value eB is compared with the threshold e2 in a step S39. If the general pattern values eA, eB are smaller than the threshold e2 in the steps S38, S39, then the quantized pattern of the detected hitting sound is not similar to either one of the registered reference patterns 22a, 22b, and is judged as being incapable of being determined, i.e., the empty can is judged as being incapable of being sorted out, in a step S40. If either one of the general pattern values eA, eB is greater than the threshold e2, then general pattern values eA, eB are compared with each other in a step S41. If eA>eB, then the empty can is determined as an aluminum can in a step S42. If not eA>eB, then the empty can is determined as an iron can in a step S43.

Mechanical structures of some of the devices that make up the can material sorting apparatus will be described below.

Figure 9:
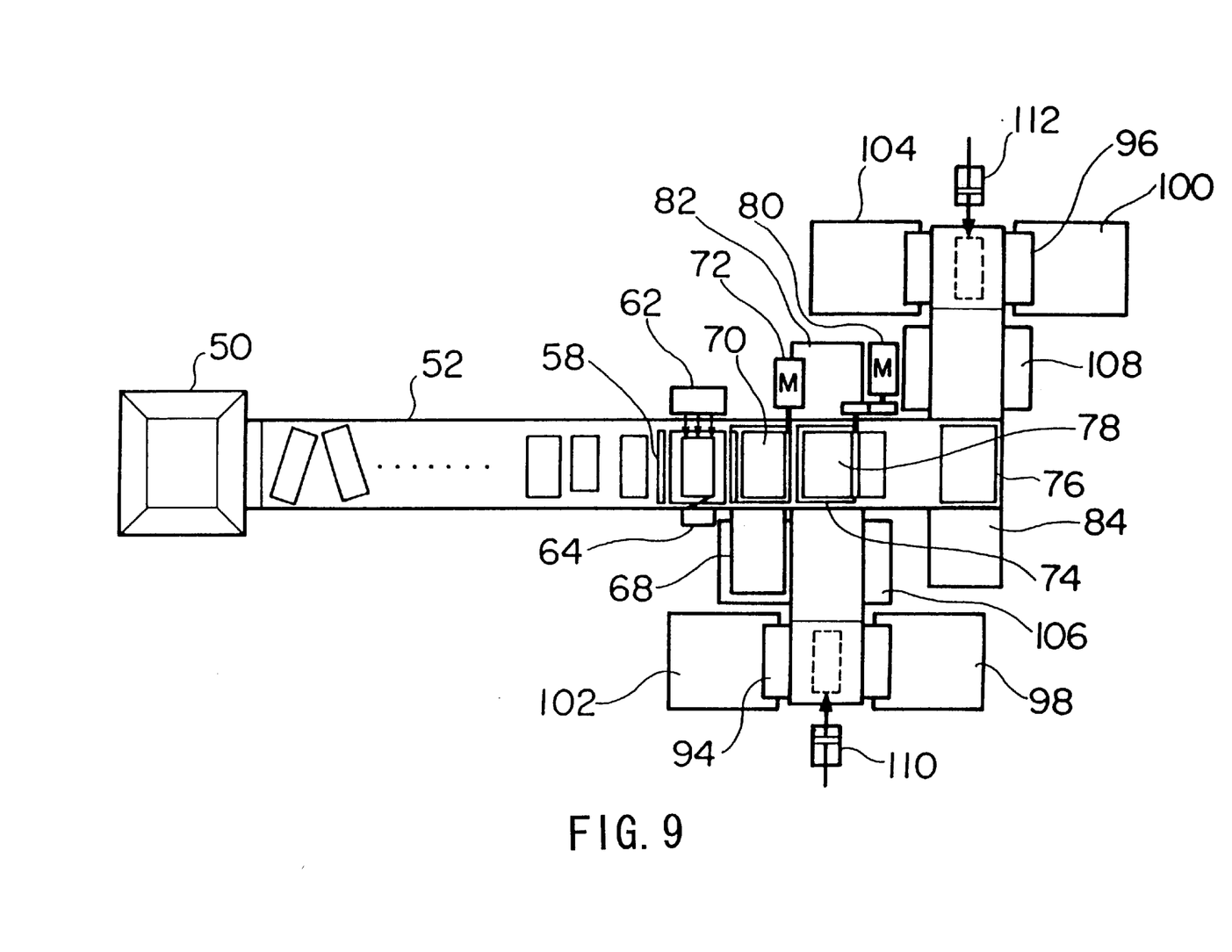
FIG. 9 is a schematic plan view of the can material sorting apparatus.
Figure 10:
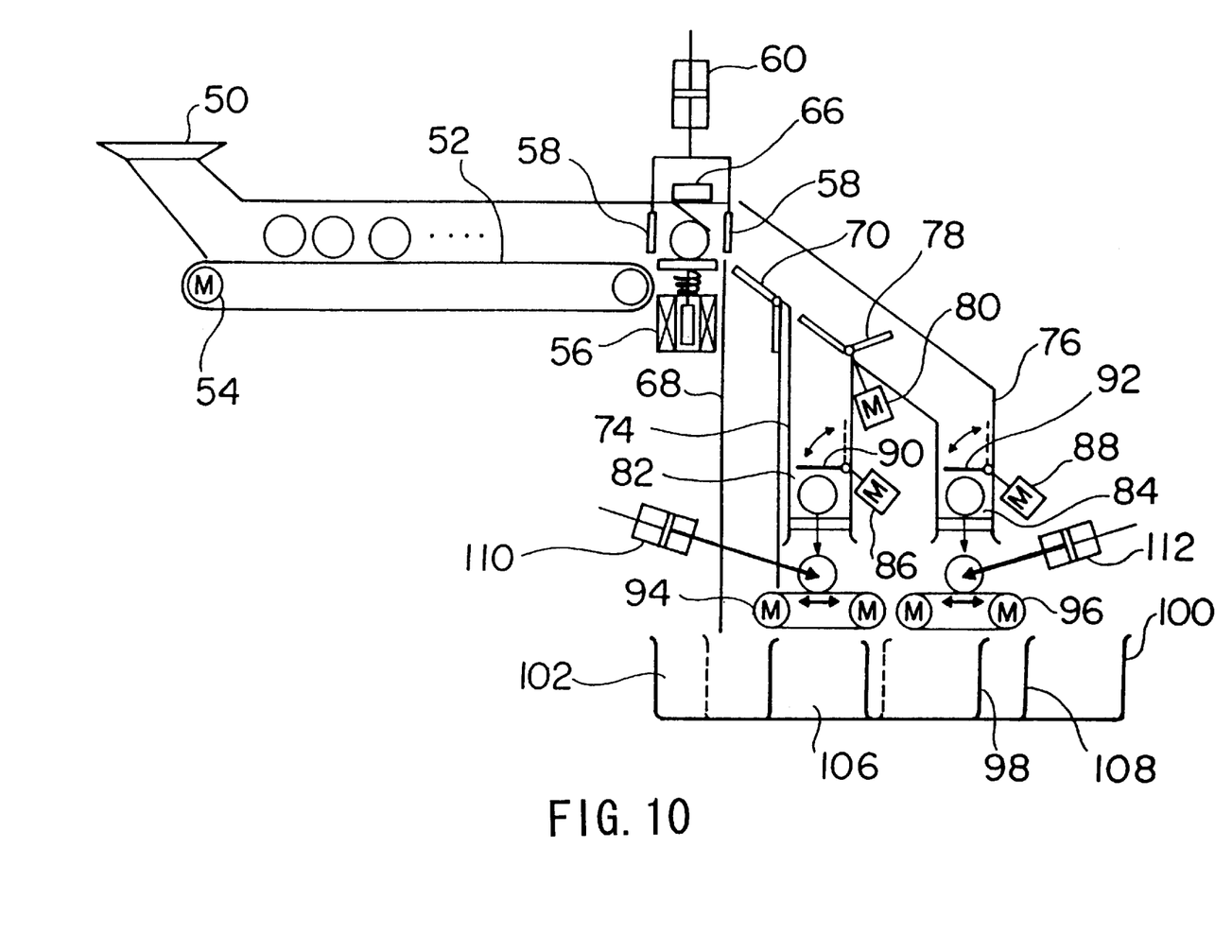
FIG. 10 is a schematic side elevational view of the can material sorting apparatus.

FIG. 9 is a schematic plan view of the can material sorting apparatus, and FIG. 10 is a schematic side elevational view of the can material sorting apparatus. As shown in FIGS. 9 and 10, the can material sorting apparatus has a can charging inlet 50 connected to a horizontal can aligning conveyor 52 that is positioned below the can charging inlet 50. The can aligning conveyor 52 is operated by a conveyor motor 54, and serves as the can aligner 10 for aligning empty cans of aluminum and iron that are charged from the can charging inlet 50, while transferring the empty cans. A can inspection table positioned downstream of the can aligning conveyor 52 comprises a weight detector 56 in the form of a differential transformer, a shutter 58 for introducing one empty can at a time from the weight detector 56, an air cylinder 60 for vertically moving the shutter 58, an optical sensor 62 for detecting the apertured end or bottom of an empty can placed on the weight detector 56, a limit switch 64 positioned across the weight detector 56 from the optical sensor 62, for detecting the length of an empty can placed on the weight detector 56, and a limit switch 66 positioned above the weight detector 56, for measuring the diameter of an empty can placed on the weight detector 56.

A vertical chute 68 for discharging empty cans which contain foreign matter is positioned downstream of the can inspection table, and a selector valve 70 is placed in the upper end of the vertical chute 68. The selector valve 70 is actuated by a motor 72 to selectively open and close the upper inlet of the vertical chute 68 depending on the result of inspection by the can inspection table. The can inspection table, the chute 68, the selector valve 70, and the motor 72 jointly make up the can rejecter 12.

Downstream of the selector valve 70, there are positioned two vertical chutes 74, 76 whose inlet ends are associated with a selector valve 78. When the optical sensor 62 detects the bottom of an empty can placed on the weight detector 56, the selector valve 78 is actuated by a motor 80 to open the inlet end of the chute 74 for thereby directing the empty can into the chute 74. When the optical sensor 62 detects the apertured end of an empty can placed on the weight detector 56, the selector valve 78 is actuated by the motor 80 to open the inlet end of the chute 76 for thereby directing the empty can into the chute 76. The selector valve 78 and the motor 80 jointly serve as the can direction classifier 14. The chute 74 has a lower opening connected to a can hitting device 82 and the chute 76 has a lower opening connected to a can hitting device 84. The can hitting devices 82, 84 have respective can inlets equipped with respective sound-resistant doors 90, 92 actuatable by respective motors 86, 88, and respective can outlets associated with respective sorting conveyors 94, 96. Aluminum can storage box 98 and iron can storage box 102 are disposed respectively below opposite ends of the sorting conveyor 94, and aluminum can storage box 100 and iron can storage box 104 are disposed respectively below opposite ends of the sorting conveyor 96. Rejected can boxes 106, 108 are disposed on one side of the respective sorting conveyors 94, 96. Air cylinders 110, 112 are disposed on the other side of the respective sorting conveyors 94, 96 remotely from the rejected can boxes 106, 108. The chute 68 has a lower end opening over the rejected can box 106 for discharging rejected cans into the rejected can box 106. Depending on the results of analysis and pattern comparison of hitting sounds produced by the can hitting devices 82, 84, the sorting conveyors 94, 96 and the air cylinders 110, 112 operate to deliver empty cans into the aluminum can storage boxes 98, 100 or the iron can storage boxes 102, 104 and discharge rejected empty cans into the rejected can boxes 106, 108. The sorting conveyors 94, 96 and the air cylinders 110, 112 jointly serve as the can sorting device 40.

When empty cans are charged into the can charging inlet 50, the empty cans are delivered by the conveyor 52 and directed perpendicularly to the conveying direction of the conveyor 52 so as to be aligned in an array. The aligned empty cans are then successively transferred, one by one, into the can inspection table. When the shutter 58 is moved upwardly by the air cylinder 60, an empty can is placed onto the can inspection table. When the shutter 58 is moved downwardly by the air cylinder 60, the empty can starts being inspected. The diameter of the empty can is measured by the limit switch 66, the length of the of the empty can is measured by the limit switch 64, the empty can is checked for foreign matter contained therein by the weight detector 56, and the empty can is checked for direction by the optical sensor 62.

The checked empty can is discharged from the can inspection table while at the same time another empty can 15 is introduced into the can inspection table with the shutter 58 being lifted upwardly by the air cylinder 60. At this time, the selector valve 70 operates according to the results of inspection by the can inspection table. Specifically, if the limit switch 66 has detected a predeter20 mined can diameter, the limit switch 64 has detected a predetermined can length, and the weight detector 56 has detected a standard can weight, then the selector valve 70 closes the upper inlet of the chute 68. If the limit switch 66 has not detected a predetermined can diameter, the limit switch 64 has not detected a predetermined can length, or the weight detector 56 has not detected a standard can weight, then the selector valve 70 opens the upper inlet of the chute 68. Therefore, an empty can that is judged as having a different size or weight on the can inspection table is an empty can for which no reference patterns are registered in the reference pattern registering device 22 or which contains foreign matter, and is determined as being incapable of being sorted out. The empty can thus determined is discharged into the rejected can box 106 by the chute 68, and will not be hit for analysis of hitting sounds.

If an empty can is determined as being capable of being sorted out based on an analysis of a hitting sound, then when the empty can is discharged from the can inspection table, the selector valve 78 has been changed in its angular position based on the result of measurement by the optical sensor 62. Specifically, if the optical sensor 62 has detected the bottom of the empty can, then the selector valve 78 opens the inlet of the chute 74 to guide the empty can into the chute 74, and if the optical sensor 62 has detected the apertured end of the empty can, then the selector valve 78 opens the inlet of the chute 76 to guide the empty can into the chute 76. When the empty can is supplied to either one of the can hitting devices 82, 84 through the corresponding one of the chutes 74, 76, the corresponding one of the sound-resistant doors 90, 92 is closed, and the empty can is hit by the can hitting device 82 or 84, producing a hitting sound. The hitting sound is picked up, analyzed by the short-time FFT analyzer 34, and converted into a pattern by the pattern generator 36. The pattern is compared with the reference patterns 22a, 22b by the pattern matching device 38. The result of comparison is supplied to the can sorting device 40 to determine the direction in which to operate the sorting conveyors 94, 96 and whether the air cylinders 110, 112 are to operate. Inasmuch as empty cans are processed selectively in two sorting systems depending on the direction in which they face, the charged empty cans are processed simultaneously by the two sorting systems. Therefore, the can material sorting apparatus can process supplied empty cans in a relatively short period of time.

Figure 11:
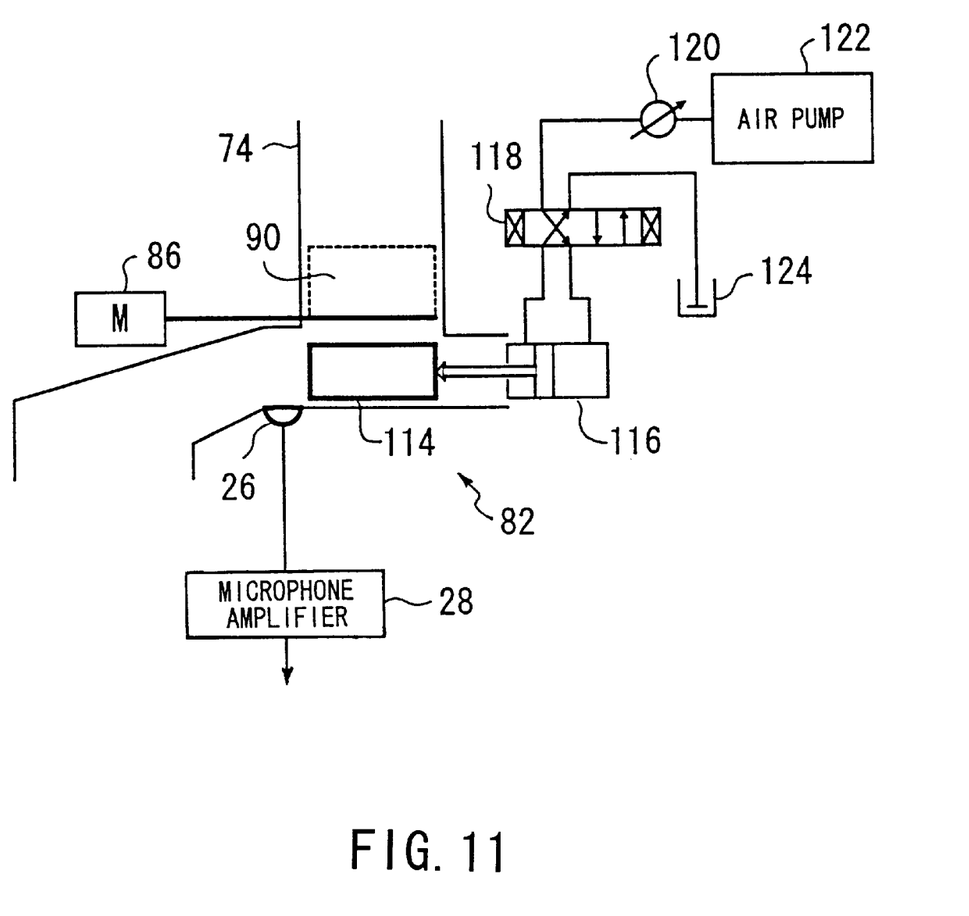
FIG. 11 is a schematic view of a can hitting device.

FIG. 11 schematically shows one of the can hitting devices 82, 84. Since the can hitting devices 82, 84 are identical to each other, the can hitting device 82 will be described below. As shown in FIG. 11, the can hitting device 82 has the sound-resistant door 90 for closing an inlet of the can hitting device 82 after a can 114 is supplied to the can hitting device 82 through the chute 74, the motor 86 for actuating the sound-resistant door 90, and an air cylinder 116 positioned so as to face the bottom of a can supplied to the can hitting device 82. The air cylinder 116 is connected to a two-way directional control valve 118 having an air supply port connected through a pressure regulating valve 120 to an air pump 122 and an air discharge port connected to a damper 124. The microphone 26 for detecting a hitting sound is disposed at an outlet of the can hitting device 82. The microphone 26 has an output terminal connected to the microphone amplifier 28.

The can hitting device 82 produces a hitting sound by hitting the bottom of the can 114 with a hammer head mounted on the tip end of the piston rod of the air cylinder 116. After hit by the hammer head, the can 116 is pushed out of the can hitting device 82 onto the sorting conveyor 94. The force with which the can 116 is pushed can be varied by adjusting the pressure regulating valve 120. The hitting sound produced by the can 114 is picked up by the microphone 26, and a sound signal generated by the microphone 26 is supplied through the microphone amplifier 28 to the short-time FFT analyzer 34, which analyzes the sound signal.

In the illustrated embodiment, only one can size has been described. However, since can diameters and lengths are checked in the pre-processing operation of the can material sorting apparatus, different can sizes may be determined and reference patterns for those different can sizes may be registered, so that even if inspected empty cans have different sizes, their materials may be recognized to sort out aluminum and iron cans. While the short-time FFT analyzer is employed to analyze hitting sounds in the disclosed embodiment, there may be used an analyzer which employs a Wigner distribution function or a wavelet transformation and which takes more time than the short-time FFT analyzer but has higher selectivity.

In the above preferred embodiment, the present invention is applied to sort out empty cans according to their material. However, the principles of the present invention are also applicable to any articles which can produce characteristic sounds when they are hit.

With the present invention, as described above, a hitting sound generated by the hitting sound generating means when an article is hit is detected by the sound detecting means and analyzed by the detected-sound analyzing means. The analyzed result is converted into a pattern by the detected-sound pattern generating means, and the pattern is matched with registered reference patterns from the reference pattern registering means by the pattern matching means. Based on the result of matching, the article is sorted out by the article sorting means. Therefore, it is possible to detect the material of a container which cannot be determined according to its appearance, such as cans of aluminum and iron which are identical in shape and size to each other. It is also possible to check the amount of a filling in a container that cannot directly be seen, sort out objects that cannot be sorted out by other sorting apparatus, e.g., a vegetable or fruit such as watermelon according to its ripeness, or inspect baked articles for pores contained therein.

Furthermore, because a signal necessary for analysis is a sound signal, the detecting device for detecting such a sound signal may comprise a microphone and an amplifier. Thus, the detecting device is much simpler than those used in other sorting apparatus.

The foregoing is considered as illustrative only of the principles of the present invention. Further, since numerous modifications and changes will readily occur to those skilled in the art, it is not desired to limit the invention to the exact construction and applications shown and described, and accordingly, all suitable modifications and equivalents may be regarded as falling within the scope of the invention in the appended claims and their equivalents.

What is claimed is:

1. An article inspection apparatus comprising:
    a hitting sound generating device hitting an article to generate a hitting sound;
    an article identifying device identifying the article based on the hitting sound generated by said hitting sound generating device;
    a sound detecting device detecting the generated hitting sound;
    a detected-sound analyzing device analyzing the detected sound;
    a detected-sound pattern generating device converting the analyzed sound into a pattern;
    a reference pattern registering device generating and registering a reference detected-sound pattern;
    a pattern matching device comparing the pattern generated by said detected-sound pattern generating device with the reference detected-sound pattern registered by said reference pattern registering device to determine whether the generated pattern is similar to the reference detected-sound pattern; and
    said detected-sound pattern generating device comprises dividing a plane formed of frequencies and time into a plurality of segments and converting frequency levels of the detected sound which correspond respectively to said segments into numerical values for thereby generating said pattern.

2. An article inspection apparatus according to claim 1, further comprising an article sorting device sorting out the article into a position depending on the result of identification by said article identifying device.

3. An article inspection apparatus according to claim 1, further comprising a sound resistant device surrounding the article.

4. An article inspection apparatus according to claim 1, wherein said sound detecting device comprises:
    a microphone picking up the hitting sound;
    a microphone amplifier amplifying a sound signal produced by said microphone; and
    a noise removing circuit removing background noise from the sound signal.

5. An article inspection apparatus according to claim 1, wherein said detected-sound analyzing device determines frequency levels of the detected sound continuously in time.

6. An article inspection apparatus according to claim 1, wherein said pattern matching device determines differences between numerical values of the segments of said pattern of the detected sound and said reference detected-sound pattern, and evaluating agreement between said pattern of the detected sound and said reference detected-sound pattern based on the sum of said differences.

7. An article inspection apparatus according to claim 1, further comprising a pre-processing device determining whether an article supplied to said hitting sound generating device can be inspected or not.

8. An article inspection apparatus comprising:
    a generating device causing an article to emit a sound;
    a pattern generating device converting the sound into a pattern by dividing a plane formed of frequencies and time into a plurality of segments and converting frequency levels of the detected sound which correspond respectively to said segments into numerical values for thereby generating said pattern; and
    a pattern matching device identifying the article using said generated pattern.

9. The article inspection apparatus of claim 8, wherein said pattern matching device converts the detected sound into a pattern by determining differences between numerical values of the segments of said pattern of the detected sound and a reference detected-sound pattern, and evaluating agreement between said pattern of the detected sound and said reference detected-sound pattern based on the sum of said differences.

10. An article inspection method comprising:
    causing an article to emit a sound;
    converting the sound into a pattern by dividing a plane formed of frequencies and time into a plurality of segments and converting frequency levels of the detected sound which correspond respectively to said segments into numerical values for thereby generating said pattern; and
    identifying the article using said generated pattern.

11. The article inspection method of claim 10, wherein the identifying is performed by determining differences between numerical values of said segments of said pattern of the detected sound and a reference detected-sound pattern, and evaluating agreement between said pattern of the detected sound and said reference detected-sound pattern based on the sum of said differences.

12. A computer readable storage media comprising a computer implemented article inspection method, said article inspection method comprising:
    causing an article to emit a sound;
    converting the sound into a pattern by dividing a plane formed of frequencies and time into a plurality of segments and converting frequency levels of the detected sound which correspond respectively to said segments into numerical values for thereby generating said pattern; and
    identifying the article using said generated pattern.

13. The computer readable storage media of claim 12, wherein
    the identifying is performed by determining differences between numerical values of said segments of said pattern of the detected sound and a reference detected-sound pattern, and evaluating agreement between said pattern of the detected sound and said reference detected-sound pattern based on the sum of said differences.

* * * * *

UNITED STATES PATENT AND TRADEMARK OFFICE
CERTIFICATE OF CORRECTION

PATENT NO. : 6,026,686                                                               Page 1 of 1
DATED : February 22, 2000
INVENTOR(S) : Ichiro Hattori et al.

It is certified that error appears in the above-identified patent and that said Letters Patent is hereby corrected as shown below:

<u>Title page,</u>
Item [73], Assignee, add -- Animo Limited, Yokohama, Japan --.

Signed and Sealed this

Thirtieth Day of April, 2002

Attest:

JAMES E. ROGAN
*Attesting Officer*      *Director of the United States Patent and Trademark Office*